US009694164B2

(12) United States Patent
Hill

(10) Patent No.: US 9,694,164 B2
(45) Date of Patent: Jul. 4, 2017

(54) MEDICAL INSTRUMENT FOR INSERTING A CHEST DRAINAGE TUBE

(71) Applicant: David A. Hill, Phoenix, AZ (US)

(72) Inventor: David A. Hill, Phoenix, AZ (US)

(*) Notice: Subject to any disclaimer, the term of this patent is extended or adjusted under 35 U.S.C. 154(b) by 364 days.

(21) Appl. No.: 13/870,275

(22) Filed: Apr. 25, 2013

(65) Prior Publication Data

US 2014/0324000 A1 Oct. 30, 2014

(51) Int. Cl.
*A61B 17/28* (2006.01)
*A61M 27/00* (2006.01)
*A61B 17/34* (2006.01)

(52) U.S. Cl.
CPC ............ *A61M 27/00* (2013.01); *A61B 17/282* (2013.01); *A61B 17/2841* (2013.01); *A61B 17/3468* (2013.01); *A61M 2210/101* (2013.01)

(58) Field of Classification Search
CPC .............. A61B 17/282; A61B 17/3201; A61B 17/3415; A61B 17/2841; A61B 17/3468; A61B 1/32; A61B 17/3417; A61M 2210/101; A61M 27/00
See application file for complete search history.

(56) References Cited

U.S. PATENT DOCUMENTS

| 4,608,982 | A | * | 9/1986 | Pollard | 606/190 |
| 5,490,843 | A | * | 2/1996 | Hildwein | A61B 17/29 604/164.03 |
| 5,772,670 | A | * | 6/1998 | Brosa | A61B 17/282 606/108 |
| 5,817,072 | A | * | 10/1998 | Lampropoulos | A61M 25/0017 604/264 |
| 5,899,854 | A | * | 5/1999 | Slishman | 600/219 |
| 2002/0058965 | A1 | * | 5/2002 | Andrews | A61B 17/0206 606/205 |

* cited by examiner

*Primary Examiner* — Ryan J Severson
*Assistant Examiner* — Christian Knauss
(74) *Attorney, Agent, or Firm* — Von Hellens & Bycer Law; Matthew L. Bycer

(57) ABSTRACT

A single stage instrument is used to insert a chest drainage tube into the inter-pleural space to facilitate drainage. The instrument is scissor-like with cylinder-like channels to slidably enclose the distal section of the tube therein when closed. The tip of the instrument is curved to enter the skin incision and the offset pleural incision whereafter the instrument is rotated 180 degrees to align the curved tip with the pleural space. The curved tip facilitates sliding the chest drainage tube through the instrument to effect sufficient insertion length. Once the instrument is in place, the tube is slid along the instrument to ensure that all drainage holes in the chest drainage tube are within the pleural cavity. Thereafter, the instrument is withdrawn leaving the chest drainage tube in place. After withdrawal of the instrument, it is opened laterally for lateral disengagement with the chest drainage tube.

15 Claims, 3 Drawing Sheets

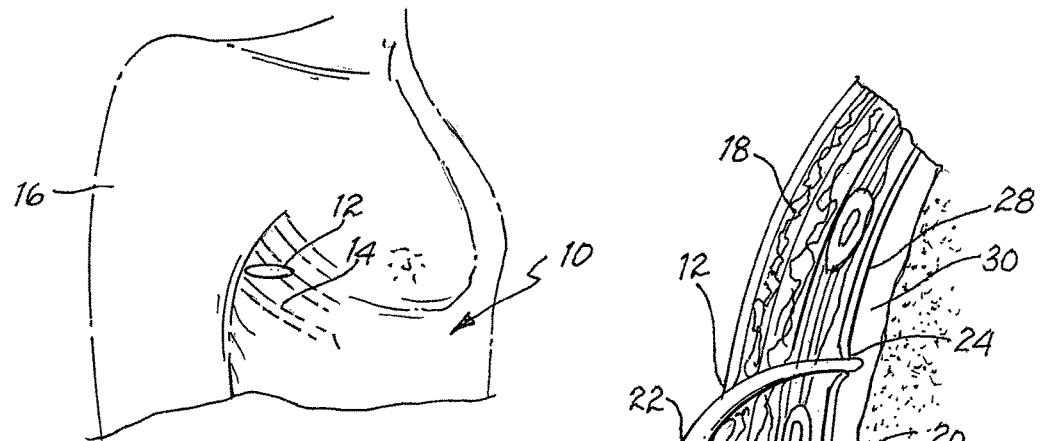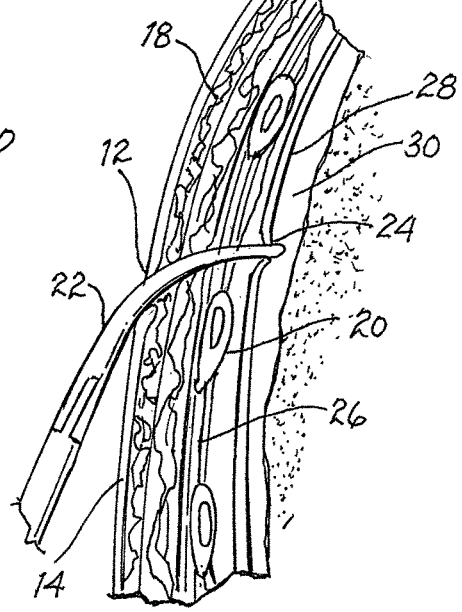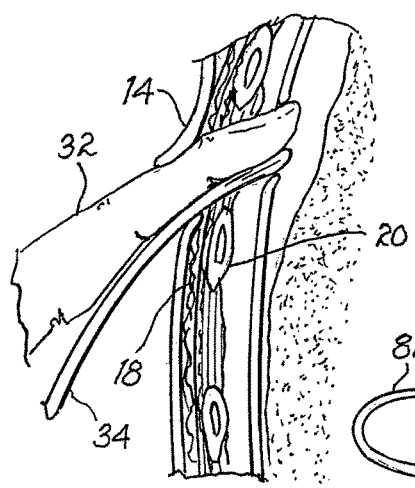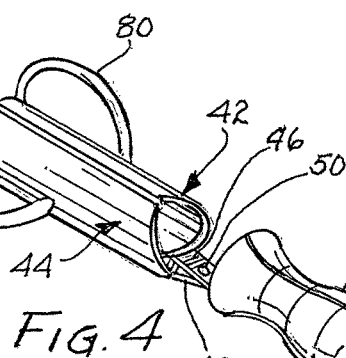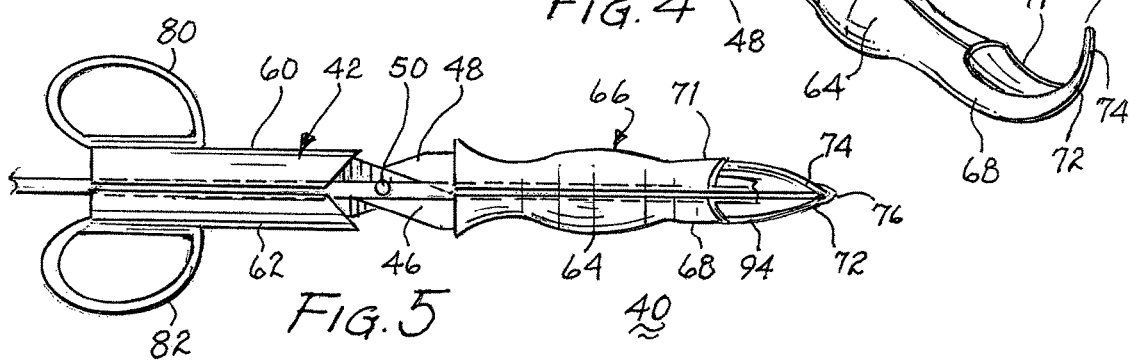

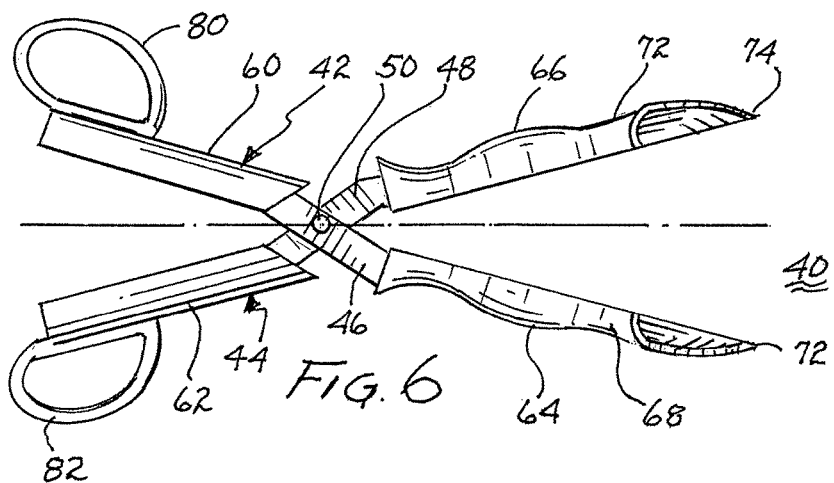
FIG. 6
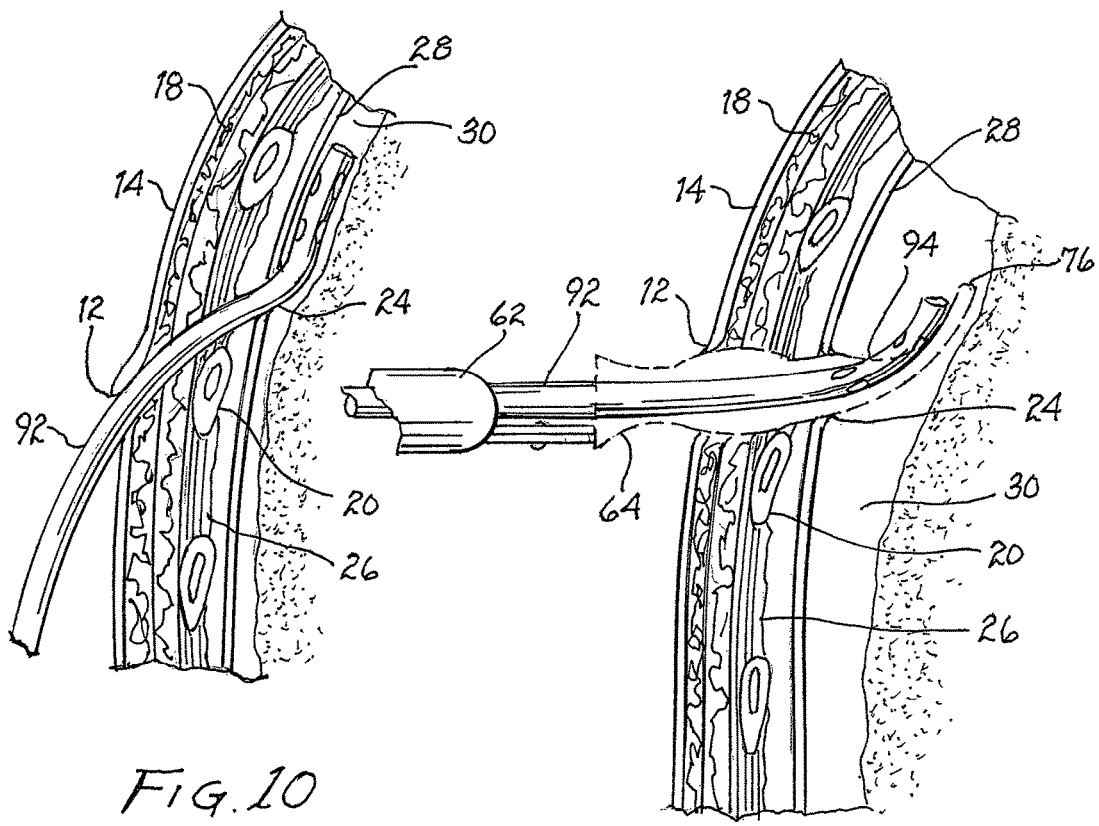
FIG. 10
FIG. 9

MEDICAL INSTRUMENT FOR INSERTING A CHEST DRAINAGE TUBE

BACKGROUND OF THE INVENTION

1. Field of the Invention

The present invention relates medical instruments and, more particularly, to an instrument for inserting a chest drainage tube.

2. Description of Related Prior Art

Conventional chest drainage tubes typically include a plurality of apertures at the distal end for inflow of fluid within the parietal pleura and effect drainage. Heretofore, the insertion of the chest drainage tube has been primarily a manual function performed by the surgeon. This operation will be summarized below to emphasize the function and utility of the present invention.

An incision is made at the level of the fifth intercostal space overlying the sixth rib. In men, this is about at the nipple line and in women it is at the level of the xiphoid process or inframammary fold. The incision is made just anterior to the mid-axillary line in a horizontal fashion.

Betadine or chlorhexidine is used as the topical antibacterial/disinfectant prior to the procedure. The chest wall is widely prepped to ensure sterility. The patient's arm on the ipsilateral side (same side as placement of the drainage tube is placed) is elevated above the patient's head to allow for adequate access. The incision is made with a scalpel of approximately 3 cm in length after injection of local anesthetic into the skin, subcutaneous tissue, and just above the rib. Once this is done, dissection through subcutaneous tissue over the rib is done with a Kelly clamp. It is important to dissect the rib above the skin incision to offset the skin incision from the pleural incision so that when the chest drainage tube is pulled out eventually, the two openings do not line up. Further blunt dissection is carried out through the intercostals muscles with the clamp, during which time it is important to keep the clamp riding along the cephalad border of the rib so as to avoid damage to the intercostals vein, artery, and nerve. These structures are collectively known as the neurovascular bundle.

The parietal pleura is then carefully punctured with the clamp tip and the opening enlarged with a gloved finger. A 360 degree sweep is made to check the visceral pleura, lung surface, and any palpable adhesions. The chest drainage tube is then inserted with a clamp on the distal end, either with the aid of a finger or by following the path previously made. A second clamp may be placed on the proximal end (outside of the patient's body) if fluid is expected so as to prevent spillage. Once inserted through the parietal pleural opening, the distal clamp may be removed and the chest drainage tube advanced apically/cephalad. The chest drainage tube is inserted to at least 12 cm to ensure that all drainage holes on the tube are within the chest. For this reason, in very large patients the insertion may be 16 cm or more, and in smaller patients the insertion may need be only 10 cm.

The proximal clamp is then removed and the end of the chest drainage tube placed in a suction canister. The position of the chest drainage tube is verified by looking for tube condensation indicating good placement. Often times, the chest drainage tube is also rotated to confirm placement as it should turn freely if not kinked.

The chest drainage tube is sutured in place with the skin with a series of knots in silk suture and the end of the chest drainage tube placed to underwater seal or suction (−20 mm water), if not already done. A chest x-ray is taken to confirm proper position and function of the chest drainage tube. If needed, the chest drainage tube can be withdrawn if too far in the chest. It is never further advanced due to the risk of introducing skin contaminants into the chest.

Hemothorax (blood in the inter-pleural space) will often drain without wall suction (blood is forced out with respirations as the lung expands). Pneumothorax (air in the inter-pleural space) requires suction until no air leak remains.

SUMMARY OF THE INVENTION

The conventional procedure for inserting a chest drainage tube into the pleural cavity requires significant manual dexterity for the surgeon to use his/her finger and a clamp to manipulate the chest drainage tube into place. This procedure may be more or less time-consuming depending upon innumerable factors. By using the instrument described herein, the insertion of the chest drainage tube is primarily a mechanical function easily and rapidly performed. The instrument circumscribes the chest drainage tube during insertion and includes a tip for penetration after insertion through the initial incision. A ramp at the distal end of the chest drainage tube causes the chest drainage tube to bend into alignment with the pleural cavity upon sliding movement of the chest drainage tube through the instrument. After placement of the chest drainage tube, the instrument is withdrawn and opened to accommodate lateral withdrawal of the chest drainage tube from within the instrument. Subsequently, the chest drainage tube may be sutured in place.

It is therefore a primary object of the present invention to provide an instrument for mechanically inserting a chest drainage tube into the pleural cavity.

Another object of the present invention is to provide an instrument for bending a chest drainage tube during insertion of the chest drainage tube into alignment with the pleural cavity.

Still another object of the present invention is to provide an instrument that is openable to accommodate lateral insertion of a chest drainage tube and closeable to permit sliding movement of the chest drainage tube therethrough.

Yet another object of the present invention is to provide an instrument slidable along a chest drainage tube after insertion and openable to accommodate lateral withdrawal of the chest drainage tube from therewithin.

A further object of the present invention is to provide an instrument having finger grips for manipulating the instrument during insertion of a chest drainage tube and withdrawal of the instrument.

A still further object of the present invention is to provide a method for using an instrument to insert a chest drainage tube within the pleural cavity.

A yet further object of the present invention is to provide a method for reducing the level of manual skills required to insert a chest drainage tube into the pleural cavity.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates the incision to be made in the torso of a patient;

FIG. 2 illustrates the use of a surgeon's finger to assist in inserting a chest drainage tube into the pleural cavity;

FIG. 3 illustrates the use of a clamp to perform a conventional procedure for inserting a chest drainage tube into the pleural cavity;

FIG. 4 is an isometric view of an instrument for inserting a chest drainage tube into the pleural cavity;

FIG. 5 is a top view of the instrument in the closed position;

FIG. 6 is a top view of the instrument in the open position during insertion and withdrawal of a chest drainage tube;

FIG. 9 illustrates the process of using the instrument to slidably insert the chest drainage tube; and FIG. 10 illustrates the inserted chest drainage tube after withdrawal of the instrument.

DESCRIPTION OF THE PREFERRED EMBODIMENT

Figure 7:
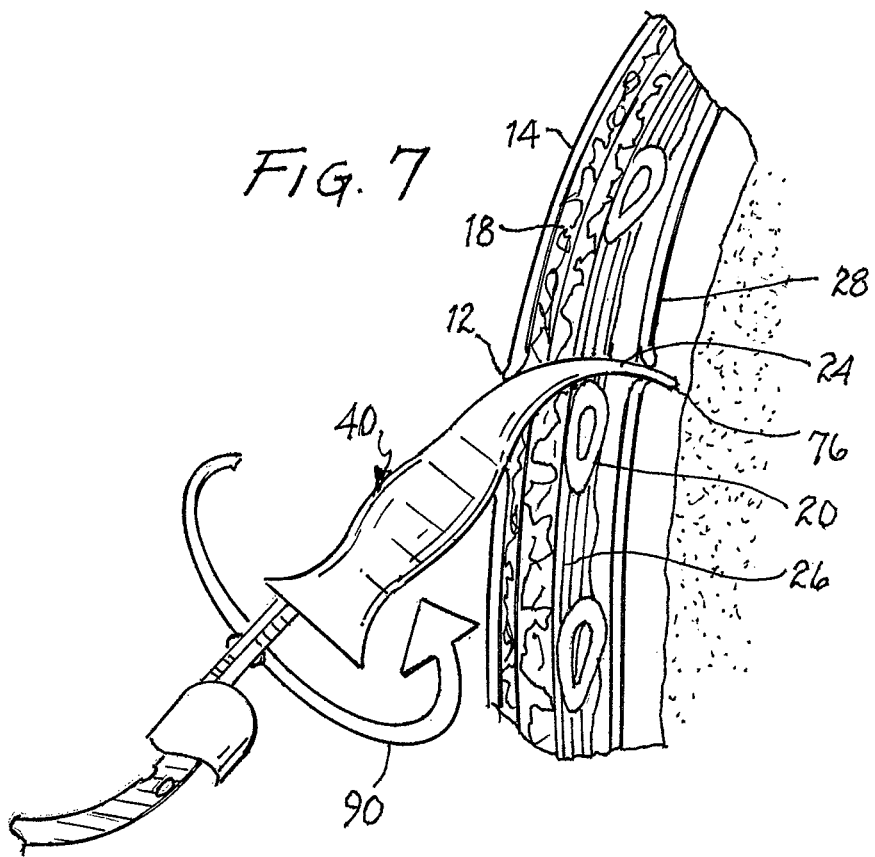
FIG. 7 illustrates insertion of the tip of the instrument followed by 180 degree rotation of the instrument.

Referring to FIGS. 1 and 2, there is shown a torso 10 of a man prior to insertion of a chest drainage tube in the pleural cavity. An incision 12 is made through skin 14 at the level of the fifth intercostal space overlying the sixth rib. The incision is made just anterior of the mid-axillary line in a horizontal fashion. The patient's arm 16 is elevated above the patient's head to allow for adequate access. The incision is 3 cm in length after injection of local anesthetic into skin 14, subcutaneous tissue 18, and just above rib 20. Once this is done, dissection through subcutaneous tissue 18 over rib 20 is done with a Kelly clamp 22.

It is important to dissect the rib above incision 12 to offset this incision from the pleural incision 24 so that the two incisions do not line up when the chest drainage tube is pulled out. Further blunt dissection is carried out through intercostal muscles with clamp 22 and it is important to keep the clamp riding along the cephalad border of rib 20 to avoid damage to the intercostals vein, artery, and nerve. These structures are collectively referred to as the neurovascular bundle.

Parietal pleura 28 is punctured with the tip of clamp 22. As particularly shown in FIG. 3, incision 24 is enlarged with a gloved finger 32. The chest drainage tube 34 is then inserted with clamp 22 on the distal end either with the aid of a finger, as shown in FIG. 3, or by following the path previously made. Once chest drainage tube 34 is inserted through parietal pleura opening 24, the distal clamp may be removed and the chest drainage tube advanced apically/cephalad.

This complex procedure is carried out more simply and more conveniently with instrument 40 shown in FIG. 4. In describing the structure of this instrument, reference will also be made to the top view of the instrument in the closed position, as shown in FIG. 5, and the top view of the instrument in the open position, as shown in FIG. 6. Instrument 40 includes two essentially mirror image elements 42, 44 pivotally connected through lands 46, 48, respectively, with a pivot 50. Element 42 includes semi-circular channel 60 (first channel) extending proximally from land 46. Similarly, element 44 includes a semi-circular channel 62 (second channel) extending proximally from land 48. The longitudinal openings of these channels face one another when in the closed position, as shown in FIG. 5, to form a tube or cylindrical enclosure.

A further channel 64 (third channel) extends from land 46. This channel is also semi-cylindrical but including different radius along the channel to provide an undulating exterior surface. A further channel 66 (fourth channel) extends from land 48. This further channel is also semi-cylindrical and has varying radii to provide an undulating exterior surface, as illustrated. Upon closure of instrument 40, as depicted in FIG. 5, further channels 64 and 66 define an essentially circular passageway therebetween, such as a tube or cylinder. A portion of side 68 of further channel 64 is cut away toward end 72 and forms a lateral opening, as illustrated in FIG. 5. Additionally, the remaining portion of side 68 toward end 72 is bent upwardly, as depicted in FIG. 4. Side 71 of further channel 66 also includes a cutaway toward end 74 to form a lateral opening, as depicted in FIG. 5. As with end 72, end 74 is bent upwardly in mating configuration with end 72 to form tip 76, as depicted in FIG. 4. To assist in manipulating instrument 40, finger grips 80, 82 may be attached to channels 62, 64, respectively. By using these finger grips, instrument 40 may be opened and closed at will to perform the procedure.

Figure 8:
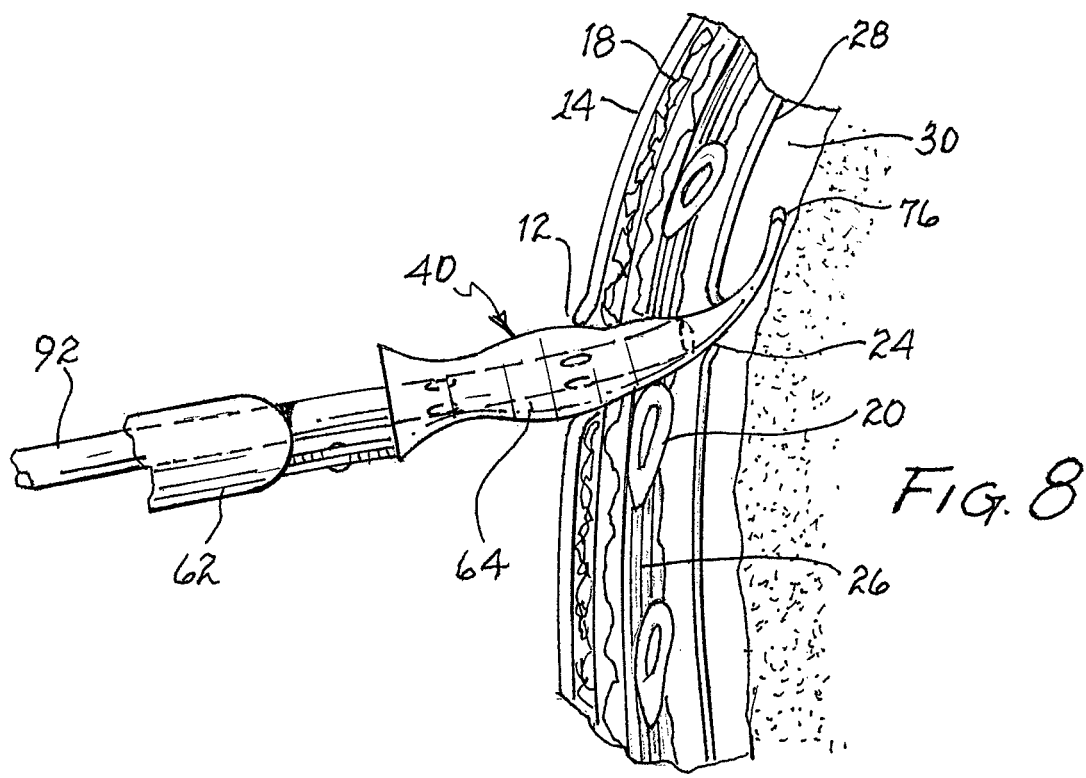
FIG. 8 illustrates the position of the instrument relative to the pleural cavity prior to insertion of the chest drainage tube.

Referring jointly to FIGS. 7, 8, 9 and 10, the above-described essentially manual procedures may be duplicated by use of instrument 40. Tip 76 of instrument 40 is inserted through incision 12 with further insertion as described above until pleural incision 24 is made. Thereafter, instrument 40 is rotated approximately 180 degrees, as depicted by arrow 90. As a result, the orientation of further channels 64, 66 and tip 76 of instrument 40 will be as depicted in FIG. 8. Thereafter, chest discharge tube 92 is slid through channels 60, 62, of which only channel 62 is depicted, and further channels 64, 66, of which only channel 64 is depicted, in the side view shown in FIG. 8.

As chest discharge tube 92 is slid further through instrument 40, it becomes curved by the guidance provided by ends 72, 74 defining outlet aperture 94, as particularly shown in FIG. 9. Such bending of the chest discharge tube essentially aligns it with the pleural cavity after a sufficient length of the chest discharge tube has been slid into the pleural cavity.

As shown in FIG. 10, instrument 40 has been withdrawn by sliding it proximally along the chest discharge tube. When clear of incision 12, instrument 40 is opened, as depicted in FIG. 6, and the instrument may be laterally moved to disengage it from the chest discharge tube. Suturing of the chest discharge tube and other medical procedures attendant the chest discharge tube may then be carried out without interference from instrument 40.

I claim:

1. A scissor-like instrument for inserting a chest drainage tube into a pleural space of a patient, said instrument comprising:
   (a) first and second mirror image elements;
   (b) a pivot for pivotally attaching said first and second mirror image elements to one another and for accommodating pivotal movement of said first and second elements from a closed position to an open position;
   (c) each of said first and second mirror image elements including:
      i) a finger grip for receiving a thumb or a finger;
      ii) a channel supporting said finger grip extending toward said pivot and having an opening oriented toward an other channel of said first and second mirror image elements;

iii) a further channel extending away from said pivot toward the distal end, said further channel defining a generally half cylinder shape having varying radii to provide an undulating exterior surface, and an opening oriented toward an other further channel of said first and second mirror image elements;

iv) one side of said further channel being tapered toward an edge of an other side of said further channel to form a tapered section terminating at an end, said tapered section being curved toward said end to form one half of a ramp;

(d) a tube formed by said channels of said first and second mirror image elements when said first and second elements are in the closed position to guide and permit passage therewithin of the chest drainage tube therethrough;

(e) a further tube formed by said further channels of said first and second mirror image elements when said first and second mirror image elements are in the closed position to guide and permit passage therewithin of the chest drainage tube therethrough; and (f) said one side of each of said further channels collectively defining a tip, a curved ramp and a laterally oriented outlet channel for providing an egress for the chest drainage tube and for bending the chest drainage tube during translation of the chest drainage tube within said instrument when said first and second elements are in the closed position.

2. The instrument as set forth in claim 1 wherein said finger grip is disposed on the proximal end of each of said first and second mirror image elements for manipulating said first and second element.

3. The instrument as set forth in claim 1 wherein each undulating surface of said further channels defines at least two distinct bulged regions separated by a narrow region therebetween.

4. The instrument as set forth in claim 3 wherein each of said channels defines a generally half cylinder shape and a cylinder for sliding passage of the chest drainage tube therethrough when said instrument is pivoted to the closed position.

5. The instrument as set forth in claim 1 wherein each of said channels define a generally half cylinder shape and a cylinder for sliding passage of the chest drainage tube therethrough when said scissor-like instrument is pivoted to the closed position.

6. The instrument as set forth in claim 1 wherein each of said further channels comprises a proximal angled flange.

7. An instrument for inserting a chest drainage tube into a pleural space of a patient, said instrument comprising:
(a) first and second channels defining a first split passageway therethrough for the chest drainage tube;
(b) third and fourth channels defining a second passageway unrestricted therethrough for the chest drainage tube, said third and fourth channels adapted for insertion into intercostal tissue, each channel of said third and fourth channels having varying radii including at least a first proximal swell and a second distal swell said first and second swells separated by a groove adapted to engage a rib and further including a distal tapered end defining one part of a lateral opening; and
(c) a tapered ramp terminating in a tip and defined by said distal tapered ends of said third and fourth channels for bending the chest drainage tube during translation of the chest drainage tube through said first passageway and said second passageway and through the lateral opening toward and past said tip.

8. The instrument as set forth in claim 7 wherein each of said first and second channels are semi-cylindrical.

9. The instrument as set forth in claim 8 wherein said first proximal swell comprises a first radius, said second distal swell defines a second maximum radius, said groove defines a third minimum radius, and wherein said third minimal radius is less than said first and said second maximum radii.

10. The instrument as set forth in claim 7 wherein each of said third and fourth channels are generally cylindrical.

11. The instrument as set forth in claim 7 wherein said distal tapered end of each of said third and fourth channels define, in combination, the lateral opening for passage therethrough of the chest drainage tube.

12. An instrument for inserting a chest drainage tube into a pleural space of a patient, said instrument comprising:
(a) first and second channels defining a first passageway therethrough for the chest drainage tube;
(b) third and fourth channels defining a second passageway unrestricted therethrough for the chest drainage tube, each channel of said third and fourth channels having varying radii including at least a first proximal swell and a second distal swell said first and second swells separated by a groove and further including a distal tapered end defining one part of a lateral opening; and
(c) a tapered ramp terminating in a tip and defined by said distal tapered ends of said third and fourth channels for bending the chest drainage tube during translation of the chest drainage tube through said first passageway and said second passageway and through the lateral opening toward and past said tip;
wherein said first and third channels are connected by a first land, said second and fourth channels are connected by a second land and a pivot interconnecting said first and second lands for opening and closing said instrument.

13. The instrument as set forth in claim 12 wherein said first and second channels generally define a cylinder when said instrument is in the closed position for sliding passage of the chest drainage tube therethrough.

14. The instrument as set forth in claim 12 wherein each of said third and fourth channels define a generally cylindrical shape having varying radii for passage of the chest drainage tube therethrough.

15. The instrument as set forth in claim 12 including first and second finger grips extending from said first and second channels, respectively, for manually pivoting said first and third channels relative to said second and fourth channels.

* * * * *